United States Patent [19]
Pfleiderer

[11] 3,932,221
[45] Jan. 13, 1976

[54] IMMUNOLOGICAL ISOZYME DETERMINATION METHOD

[75] Inventor: Gerhard Pfleiderer, Witten, Germany

[73] Assignee: Merck Patent Gesellschaft mit beschrankter Haftung, Darmstadt, Germany

[22] Filed: June 9, 1972

[21] Appl. No.: 261,215

[30] Foreign Application Priority Data
June 9, 1971   Germany............................ 2128670

[52] U.S. Cl................ 195/103.5 R; 195/99; 424/2; 424/12
[51] Int. Cl.²......................................... G01N 31/14
[58] Field of Search .......... 195/103.5, 99; 424/2, 12

[56] References Cited
UNITED STATES PATENTS
3,817,837   6/1974   Rubenstein et al. .......... 195/103.5 R

OTHER PUBLICATIONS

McGeachin et al., Serological Differentiation of Amylase Isozymes. Ann. N.Y. Acad. Sci. Vol. 94 1961 (pp. 996–1003).
Nisselbaum, et al., Reactions of Human Tissue Lactic Dehydrogenases with Antisera to Human Heart and Liver Lactic Dehydrogenases. J. of Biol. Chem. Vol. 236 No. 2 1961 (pp. 401–404).
Wilkinson, J. H., Clinical Applications of Isoenzymes, Clinical Chemistry. Vol. 16, No. 9, 1970 (pp. 733–739).
Markert, et al., Immunochemical Properties of Lactate Dehydrogenase Isozymes, Annals New York Academy of Sciences, 103, 1963 (pp. 915–929).
Wuest, et al., Isozymes of Lactic Dehydrogenase and its Thermal Inactivation in the Diagnosis of Internal Maladies, Vol. 58, Chemical Abstracts 1963 (p. 11829h).
Nisselbaum et al., Immunochemical Studies of Human Lactic Dehydrogenases, Annals New York Academy of Sciences, 103, 1963 (pp. 930–937).

*Primary Examiner*—David M. Naff
*Attorney, Agent, or Firm*—Millen, Raptes & White

[57] ABSTRACT

This invention relates to a process, to a diagnostic agent employed therein and to the use thereof, for the organ-specific and/or disease-specific diagnosis of the isozyme pattern of an enzyme occurring in multiple molecular configurations in a sample of human body fluids, tissue extracts or excretions, wherein total enzyme activity is quantitatively measured employing a conventional agent for the determination of enzyme activity, which comprises selectively forming an isozyme-antibody complex of a diagnostically relevant isozyme of the isozyme pattern of the enzyme present in the sample by employing a homologous antisera against the same human isozyme in a form free from the immunological activity of other isozymes of the same enzyme, separating the thus-formed isozyme-antibody complex substantially quantitatively, and measuring residual enzyme activity of the enzyme present in the sample.

22 Claims, No Drawings

IMMUNOLOGICAL ISOZYME DETERMINATION METHOD

BACKGROUND OF THE INVENTION

It is known that each organ or tissue possesses a specific enzyme pattern which differs to a lesser or greater degree from the enzyme patterns of other organs and/or tissues and also from those of the surrounding body fluids. In case of cell damage or tissue damage, the enzyme patterns of the surrounding body fluids usually become changed in a manner specific for the diseased organ or tissue.

These findings have been utilized in enzyme diagnostics for some time, in order to draw conclusions from the changes of the enzyme pattern in the body fluids with respect to the damaged organs and/or tissues, or with respect to the type of the disease present therein. In accordance with the usual method of enzyme diagnostics, the test fluids obtained from body fluids, e.g., whole blood, plasma, serum and liquor, from tissues, e.g., blood corpuscles, liver, kidney, muscle and brain, and from excretions, e.g., urine, stool and sputum, are examined qualitatively and/or quantitatively for the enzymatic activities present therein.

However, the results of these examinations are equivocal to a substantial extent, since the proportions of enzyme activities in many organs and/or tissues are very similar or even identical. Therefore, a genuine organ specificity of the diagnosis can be achieved only in rare cases.

In this situation, the solution suggests itself to employ the finding that several enzymes occur in multiple molecular configurations and form so-called "isozymes" for diagnostic purposes. Isozymes are formed, for example, by aldolase, hexokinase, creatine kinase and lactate dehydrogenase and by alkaline and acidic phosphatase, various transaminases (aminotransferases) and dehydrogenases. The total activity of these enzymes is the sum of the activities of their various isozymes. Although isozymes catalyze the same reaction, they possess more or less different compositions and exhibit differing physical and biochemical properties.

The concentrations of the various isozymes of an enzyme are widely different in various organs or organ structures of the human body. In individual cases, the isozymes are even strictly organ-specific. Therefore, by the determination of the isozyme pattern in body fluids, tissues or excretions, a more extensive differential diagnosis can be accomplished than by the customary determination of the enzyme pattern. However, to do so requires a quantitative determination of the individual isozyme activities of an enzyme.

The catalytic properties of the isozymes are, in most cases, so similar that a differential determination of the isozyme activities by conventional methods of enzyme activity determination is impossible. In the past, various methods have been utilized in an attempt to differentiate between the isozymes of a diagnostically important enzyme:

1. differential heat inactivation;
2. differential adsorption on sorption agents;
3. differential activity determination with various substrates; and
4. electrophoretic separation.

The methods recited under (1) through (3) do not permit a complete differentiation of the isozyme activities, so that a quantitative determination of the isozyme pattern is impossible. The method set forth under (4) permits a complete separation of the isozymes only when the isolectric points thereof are far enough apart. In any event, the quantitative determination of the isozyme activities after the separation is time-consuming and error-prone.

Therefore, it would be desirable to have available a novel method by which the isozyme activities of the diagnostically important enzymes can be quantitatively determined as a matter of routine with an accuracy sufficient for diagnostics. Such a method would constitute a significant advance in the state of the organ-specific and in the disease-specific differential diagnostic art.

A novel technique will be described hereinbelow which makes possible by simple means the determination of the various isozymes of an enzyme in a practically quantitative manner.

Methods have been described which make it possible to differentiate individual isozymes of several enzymes existing in multiple molecular forms by means of a combination of enzymological and immunological methods. According to these procedures, antisera are produced against more or less purified isozymes (as antigens). However, since these immune sera are responsive not only to the antigenic isozyme, but also to contaminations by other isozymes and other proteins in the sample to be tested, they do not contain the pure antibodies against the desired isozyme, but instead contain a multitude of further antibody activities which are in a more or less close relationship to the antibody activity against the one isozyme.

Additionally, antisera have been employed which had been obtained by the immunization with animal isozyme antigens. However, since animal and human isozymes possess a more or less differing molecular structure, the thus-obtained antisera against these isozymes also differ from one another. The antisera directed against animal isozymes are not absolutely specific with respect to the human isozymes, so that in diagnostic investigations on humans, it is impossible to obtain a quantitative impression of the isozyme pattern of an enzyme of interest.

In some of the conventional methods, it has been impossible to attain a flawless selective precipitation between isozyme (antigen) and the homologous antisera, so that inhibition of the enzymatic activity by the antigen-antibody complex had to be used for determining the antigen-antibody complex. However, in these inhibition methods, the antigen-antibody complex remains in the test serum. Such antigen-antibody complexes can also possess enzymatic activity. Thus, the immunosuppression normally cannot be rendered quantitative. Consequently, certain systematic errors, which are difficult to exclude and thus also difficult to estimate, are incurred in these determinations.

Attempts have also been made to cause the precipitation of the non-precipitable isozyme-antibody complexes by adding an excess of antiserum for complex formation with the isozyme (antigen) and then precipitating the entire complex, together with all other γ-globulins, with anti-γ-globulin sera. However, in contrast to the diagnostic method of this invention, this procedure requires a further quantitative predetermination of the titel of γ-globulins, so that exactly equivalent amounts of anti-γ-globulin can be added to the complex. Also, the reaction with the anti-γ-globulin serum requires longer reaction times, e.g., approximately 12 hours, and thus is less suitable for the practice of routing diagnostics.

The methods known heretofore generally exhibited the disadvantage that they detected only a minor portion of the isozymes of an enzyme occurring in multiple molecular forms. For example, one could merely determine in practice that, in case of certain diseases, the total activity of an enzyme was more or less eliminated by one of the isozyme antisera, without taking into account the changes in the remaining isozymes. This type of diagnosis, therefore, remained more or less empirical. Only by an analysis of all isozyme activities of the enzyme of interest is it possible to render a faultless diagnosis based on organ specificity. Such an analysis is possible only when all isozymes, or all isozymes recognized as essential to the diagnosis of the enzyme of interest, have been obtained in the pure form from humans and the corresponding specific antisera thereagainst have been produced. By means of these separate antisera, it is then possible to flawlessly decipher the total activity present in the test serum of the individual isozymes.

The results heretofore evolved in this field of research lying between enzymology and immunology could heretofore be evaluated for diagnostic purposes only with difficulty. This was due, on the one hand, to the fact that the complicacy of the described methods were complicated which made it infeasible to employ them routinely and, on the other hand, the methods had too wide a margin of error, so that the results were scarcely usable for differential diagnostics.

By means of the present invention, a reduction of complicated scientific methods to a diagnostic procedure which is realistic for practical purposes is attained, which is urgently desirable. At the same time, diagnostic accuracy is substantially increased. This result was achieved by 1. The use of pure human isozyme antigens for the preparation of specific antisera;
2. The use of practically completely precipitating antisera.
3. The use of the entire isozyme pattern for the organ-specific and/or disease-specific diagnosis, insofar as the isozymes of the pattern are relevant for an organ specificity or disease specificity of the diagnosis.

SUMMARY OF THE INVENTION

In its process aspect, this invention relates to a process for the organ-specific and/or disease-specific diagnosis of the isozyme pattern of an enzyme occurring in multiple molecular configurations in a sample of human body fluids, tissue extracts or excretions, wherein total enzyme activity is quantitatively measured, employing a conventional agent for the determination of enzyme activity, which comprises selectively forming an isozyme-antibody complex of a diagnostically relevant isozyme of the isozyme pattern of the enzyme present in the sample, employing the homologous antisera against the same human isozyme in a form free from the immunological activity of other isozymes of the same enzyme, separating the thus-formed isozyme-antibody complex substantially quantitatively, and measuring residual enzyme activity of the enzyme present in the sample.

In its composition aspect, this invention relates to a diagnostic agent for the organ-specific and/or disease-specific diagnosis of the isozyme pattern of an enzyme occuring in multiple molecular forms in human body fluids, tissue extracts or excretions which comprises a plurality of antisera each substantially completely selective as an antibody too, i.e., each recognizing only one of the human isozymes contained in the isozyme pattern of the enzyme as an antigen. In its preferred aspect, the diagnostic agent also comprises a conventional agent for the determination of enzyme activity of the enzyme.

In its method of use aspect, this invention relates to the use of the diagnostic agent of this invention for the determination of the isozyme pattern in human body fluids, tissue extracts, or excretions, respectively.

The process of this invention comprises determining, by combined enzymatic and immunological procedures, the isozyme pattern of an enzyme occurring in multiple molecular forms. Diagnostic conclusions can then be drawn from this pattern with respect to the diseased organ and/or the type of the disease. For this purpose, several antisera are first produced by immunizing suitable animals, which antisera contain precipitating antibodies against the individual isozymes. In order to ensure the optimum specificity of these antisera, the isozyme antigens employed must be of human origin and must be highly pure, as discussed hereinafter. In order to conduct the determination of the isozymes, the enzyme-containing liquid is now mixed with the antiserum against one of the isozymes, and the latter is quantitatively precipitated. The precipitate is centrifuged off after incubation. The difference between the residual activity remaining in the effluent and the previously measured total activity is the content of precipitated isozyme in the specimen. If such a determination is similarly conducted with other specific antisera against the remaining isozymes, the isozyme pattern of the sample to be tested is obtained. Thus, in any event, the preceding separation of isozymes into the individual components thereof is eliminated with.

A prerequisite for the novel determination method is that the individual isozymes are genetically defined, i.e., the synthesis thereof is controlled by different genes. In these cases, one can normally expect an immunologically detectable difference between the isozymes, which is the second requirement for the method of this invention. Immunological differentiability of the isozymes exists if the corresponding antisera do not cross-react. Therefore, another essential condition is that the antigenically effective isozymes are precipitated by the specific, homologous antisera in a practically quantitative manner. This is accomplished preferably by quantitatively precipitating antibodies, but can optionally also be achieved by several other immunological auxiliary means.

DETAILED DISCUSSION

This invention can be employed with all enzymes which exist in multiple molecular forms and the isozymes of which:

a. exhibit a different isozyme pattern in various human organs and tissues, within an organ or tissue, or within a cell;

b. can be quantitatively precipitated immunologically; and c. are subject to differing genetic control.

Among such enzymes, aldolase, hexokinase, creatine kinase, and lactate dehydrogenase are preferred.

Aldolase occurs as aldolase "A", "B", and "C" in the human body, type "A" being predominant in the cardiac and skeletal muscle, type "B" being predominant in the liver, and type "C" being predominant in the brain. Hexokinase exists as at least five different isozymes, among which two are diagnostically relevant. The hexokinase isozymes occur in the liver, muscle, brain, erythrocytes, etc. in various isozyme patterns characteristic for each organ and/or tissue. Creatine kinase consists of at least three different isozymes, viz., the muscle enzyme and the brain enzyme which differ completely from each other immunologically, and a third "intermediate form" which apparently consists of subunits of the other two isozymes. Lactate dehydrogenase is likewise known in at least five different isozymes (1–5), which can be differentiated by electrophoresis. The isozyme pattern changes from tissue to tissue. The isozymes (1 and 2) which migrate most rapidly electrophoretically are concentrated in cardiac extracts, whereas the liver and skeletal muscles contain the more slowly migrating isozyme fractions (4 and 5).

In addition to these four enzymes, other enzymes occurring in multiple molecular forms are likewise usable for the diagnostic method of this invention, for example, the various kinases, the transaminases, e.g., alanine aminotransferase and aspartate aminotransferase, the dehydrogenases, e.g., glutamate dehydrogenase, glucose-6-phosphate-dehydrogenase and malate-dehydrogenase, phosphatases, e.g., acid and alkaline phosphatases, peptidases, e.g., leucine-aminopeptidase, $\gamma$-glutamyltranspeptidase, alanine-aminopeptidase, proteases, e.g., trypsin, chymotrypsin, pepsin, other hydrolases, e.g., amylase, neuraminidase, arginase, esterases, e.g., lipase, lipoprotein lipase, cholinesterase, microsomal esterases, and nucleotidases, e.g., 5'-nucleotidase.

Broadly, the term "isozyme pattern" means the sum total of the isozymes occurring in the individual organs, tissues, body fluids and excretions of the human body. More specifically, this term defines the sum total of the diagnostically relevant isozymes of an enzyme occurring in multiple molecular configurations, i.e., the diagnostically irrelevant isozymes are excluded. Isozymes constituting less than about 10% in the total activity of the enzyme are generally irrelevant from a diagnostic viewpoint. Isozymes which cannot be detected immunologically obviously also are not included in this term.

Accordingly, diagnostically relevant isozymes are those isozymes having a proportion of more than about 10% in the total activity and which can be detected immunologically and the pattern of their activity is the diagnostically relevant isozyme pattern.

Isozymes of the human body can be isolated from both living and dead persons. In the former case, they can be obtained, for example, by operation and/or puncture. Suitable organs and/or tissues from which the isozymes can originate include, inter alia: heart, liver, kidney, spleen, lung, brain, thyroid gland, tonsil, spinal cord, blood corpuscles and muscle. When using organ and tissue samples, the samples thereof are solubilized by conventional methods, e.g., cell wall destruction, so as to provide fluid samples having enzyme activity. The distribution of the isozymes in the individual organs and/or tissues can be determined from the literature. See, for example, E. L. Coodley, "Diagnostic Enzymology", Chapter 8, pp. 223–255, (Philadelphia, Pa. 1970); J. King, "Practicl Clinical Enzymology", Chapter 8, pp. 309–341 (London 1965).

The purity of the human isozymes employed as antigens is of decisive importance for the accuracy of the reaction of this invention. This is clear if one considers that in the immunization of animals, even minimal amounts of antigen can stimulate the immune-competent cells to produce antibodies, so that the quantity of thus-produced antibodies is not necessarily in proportion to the amount of the antigen administered.

The isozyme antigens used in this invention must, therefore, be free of the immunological activities of the remaining isozymes of the enzyme under investigation. A sensitive criterion for this requirement for purity is the immunological analysis which is advantageously carried out by means of the diffusion or electrophoresis technique, which should reveal no extraneous isozymes. Additionally, for example, the methods of analytical disk electrophoresis and of polyacrylamide gel electrofocusing are useful. In the use of these methods, the demonstration of the purity with respect to the heterologous antigens is primarily of interest. In contrast thereto, the absolute purity with respect to other proteins, which purity can be determined, for example, by the two last-mentioned methods, is of lesser importance. The microheterogeneity of several isozyme types, which can manifest itself, for example, in minor differences of the amino acid composition, normally does not play any part as a criterion for purity.

Isozyme impurities detected in this way can be separated by one or more appropriate preparative method. In case of aldolase, for example, preparative electrofocusing on polyacrylamide gel in a pH range of between 7 and 10 can be employed. Also, carrier-free preparative electrophoresis is useful.

It is furthermore essential for the process of this invention to employ antisera which can be removed from the sample substantially quantitatively, preferably so that the complex-bound and precipitated isozyme can be completely removed from the analytical solution prior to the determination of residual activity. Substantially quantitatively, as used herein, means at least 90%, preferably 95–100%, of the isozyme activity is removed.

For the most part, the isozyme-antibody complexes can be sequentially removed from the sample substantially quantitatively from the sample by precipitation. However, if the complex cannot be precipitated substantially quantitatively, in certain cases the removal of the complex from the sample can be rendered more quantitative by methods known in immunology. For example, the previously purified antiserum can be adsorbed on latex particles which can be produced, for instance, from polystyrene in any desired and accurately adjusted size. The thus "applied" antibodies exhibit (together with the carrier) a higher molecular weight than the $\gamma$-globulins of the antisera by themselves, and agglutinate the isozyme more readily.

In place of the latex particles, it is also possible to employ, as the antibody carriers, i.e., supports or substrates, erythrocytes treated with a tannin (for example m-digallic acid).

The antisera are preferably obtained by the immunization with one of the isozymes of an animal yielding so-called precipitating antibodies. For this purpose, primarily suitable are vertebrates, e.g., horses, cows, sheep, dogs, pigs, including miniature pigs, rabbits, various species of monkeys gallinaceous birds, including chickens, guinea fowl, turkeys, bustards and ostriches, goose-type and duck-type birds, rats, guinea pigs, mice, etc. For the production of larger amounts of antisera, especially suitable are the larger of the above-enumerated animals. Thus, turkeys are suitably utilized, for instance, for obtaining precipitating antibodies against aldolase.

The antisera are obtained in accordance with processes generally known in immunology. Such methods are described in depth, for example, in "Methods in Immunology and Immunochemistry," Vol. 1, by C. A. Williams and M. W. Chase, Academic Press 1967. In order to raise the antibody level of the immunized animal, secondary immunizations and/or so-called "booster reactions" are, inter alia, employed as well. In the latter method, it is possible to use, for example, the so-called Freund adjuvant, representing a water-in-oil suspension optionally with the addition of certain killed mycobacteria.

The original or starting enzyme activity of the fluid sample to be tested is determined by the addition of a conventional agent, according to a standard method prior to and after the precipitation of the antigen-antibody complex.

Preferred are those determination methods of enzyme activity which are based on measurements in ultraviolet light. However, for several of the described enzymes, for example hexokinase, photometric methods are likewise feasible. Also titrimetric testing methods can be used. A collection of standard methods for enzyme determination can be found, for example, in the manual "Methoden der Enzymatischen Analyse", 2nd Ed., Vol. I, Weinheim/Bergstrasse, 1970, edited by Hans Ulrich Bergmeyer.

For the precipitation of the individual isozymes, an up to tenfold excess of the theoretical amount of the antiserum required to form an antibody-isozyme complex with all of that isozyme in the test fluid can be added to the test fluid. However, ordinarily, 2–5 times of the theoretical amount of antiserum is utilized, preferably twice the amount. Amounts of antiserum which are lower or higher than those set forth herein can result in incomplete and/or soluble immune precipitates which are both unusable for the method described herein. The antibody titer of the thus-obtained antisera can be determined with the aid of a so-called "Heidelberger" curve, a curve obtained by the titration of a specific volume quantity of antiserum with increasing amounts of isozyme (antigen) and by measuring the thusproduced turbidity values. The maximum of such a "Heidelberger" curve indicates the amount of antiserum which completely precipitates a specific amount of antigen. Since the titer of the thus-obtained antisera varies, depending on the experimental animal and the type of immunization, the antibody content of each individual antiserum or of a pool of several antisera should be determined by means of immune titration with a standardized isozyme (antigen). From this titration, the required antiserum excess can then also be readily fixed.

The practical conductance of the diagnostic method will be explained hereinbelow with reference to an isozyme determination in the serum.

First, the total enzyme activity of the particular enzyme of interest in the serum to be tested is determined in accordance with a conventional enzyme determining method, e.g., a determination procedure based on a UV-test. Thereupon, several separate specimens of the serum, e.g., a number corresponding to the diagnostically relevant isozymes, is mixed with corresponding, diagnostically relevant antisera obtained against pure human isozymes of that enzyme. The amount of antiserum added to the respective sample is approximately dependent on the titer to be expected in the sample to be tested, and is, as mentioned above, determined with the aid of a preceding titer determination of the antisera ("Heidelberger" curve).

Preferably, an approximately double excess, i.e., twice the expected theoretical amount, of the antiserum is employed. Thereafter, a sodium chloride concentration favorable for the precipitation of the antibody-antigen complex is set, which concentration can range between 0.1% and 10%, but is ordinarily 0.5–5%, particularly between 2.5% and 4%. Subsequently, an incubation is conducted for 1 minute to 5 hours, preferably 1–2 hours, at 25°–45° C., but preferably at 37° C. Then, the reaction mixture is allowed to stand for some time, for example 1–5 hours, under low-temperature conditions, for example at the temperatures ambient in a refrigerator. Finally, the precipitate is removed by centrifuging at 5,000–40,000, preferably about 20,000 revolutions per minute. The centrifuging period varies between ½ minute and 2 hours. The precipitate, however, ordinarily has settled after about 10 minutes. Subsequently, a second total enzyme determination is carried out on the supernatant to determine residual enzyme activity. The difference with respect to the initial and subsequent total enzyme activity indicates the activity of the thus-precipitated isozyme.

With several of the enzymes employed according to the present diagnostic determination method, it is possible to detect the complete isozyme pattern of the fluid to be tested. This is the case, for example, with aldolase, which occurs in three isozymes. In other enzymes occurring in multiple molecular forms, however, the totality of the various isozyme types is not yet known or is disputed in scientific circles. In such a case, it is sometimes difficult to isolate the pure isozyme types required for the immunization from humans and to prove their uniformity. Furthermore, several isozymes have only a relatively minor part in the total activity, e.g., a proportion of less than 5%. In such cases, it is advantageous to detect diagnostically only the isozymes which occur in a sufficient activity and which are accurately determined, i.e., to limit the diagnosis to these isozymes which are diagnostically relevant.

If an isozyme is, for example, organ-specific or tissue-specific, the rise in the respective isozyme activity in the serum when the respective organ or tissue is diseased, can alone be disease-specific. In such an instance, it is possible to make a diagnosis based on the one isozyme. However, normally, the situation is not as favorable, i.e., the diagnosis must be made on the basis of several diagnostically relevant isozymes.

A special problem for enzyme diagnostics on an immunological basis is represented by the so-called "hybrid isozymes." These are produced by the novel combination of subunits of differently pure isozymes in differing proportions. Since the hybrids represent composite forms between the individual, pure isozyme types, they can also be precipitated, to varying degrees, by several antisera to pure isozymes. Sometimes, in this way, enzyme activity values are simulated which are higher than the sum of the isozyme activities actually present.

If the hybrids of a certain isozyme are organ-specific, they can increase even further the interpretational capacity of the disclosed immunological diagnostic method. This is the case, for example, in aldolase which occurs in the hybrid form only in the myocardium and in the brain. A determination of the sum of the isozyme activities of this enzyme lying substantially above 100% is a clear indication of the fact that the myocardium or the brain is the organ of origin of the excess enzyme. In contrast thereto, in numerous other enzymes, e.g., hexokinase, hybrids play a lesser part and also exert a less great influence on the enzyme diagnostics. Sometimes, it is also possible for a reduction of organ specificity to occur, if hybrids occur regularly in several organs. In these cases, it is sometimes advantageous to utilize another enzyme occurring in multiple molecular forms for the organ diagnostics.

The above-described testing method is suitable not only for rather large institutions and/or clinics, capable of producing immune sera, but it can also be advantageously utilized, in the form of mass-produced testing kits, in smaller institutions and in the physician's office. A test kit of this type can, for example, contain all reagents necessary to conducting the process of this invention and consequently a test can be conducted at minimum expense. Components of such a mass-produced test kit are, for example, (a) separate antisera against at least several and preferably all diagnostically relevant isozymes of an enzyme occurring in multiple molecular forms, and (b) a reagent for determining total enzyme activity of the enzyme before and after precipitation.

Preparation and Production of the Reagents in the Pure Form:

1. Organs

Skeletal musculature, liver and brain are taken from human corpses within approximately 8-12 hours after onset of death and frozen at −20° C.

2. Isolation of the Three Types of Aldolase a. Isolation of Aldolase "A"

500 g. of human skeletal muscle is comminuted with a meat grinder and stirred together with 2 liters of ice-cold 0.01 M tris(hydroxymethyl)aminomethane buffer (tris buffer), pH 7.5. 300 Ml. portions of the mixture are homogenized at 20,000 revolutions and the homogenate is thereafter centrifuged off at 0° C. and at 13,000 g. The sediment is extracted with 1 liter of ice-cold buffer and is centrifuged at 0° C. The overflow is mixed at 0° C. with solid ammonium sulfate until a saturation of 0.30 is reached. After one hour at 0° C., the solution is centrifuged at 20,000 g., the sediment is discarded and the supernatant is brought to a saturation of 0.65 by the further addition of solid ammonium sulfate. After centrifuging, the sediment is dissolved in 200 ml. of 0.01M tris buffer and dialyzed against 10 liters of the same buffer for 24 hours. The thus-dialyzed solution is charged, for further purification, on a phosphocellulose column (40 × 500 mm.), which column has previously been equilibrated with 0.01 M tris buffer, pH 7.5. The column is washed with the buffer until no protein can be detected in the eluate. Further undesired proteins, e.g., hemoglobin, are removed by elution with 0.1M tris buffer. Finally, the aldolase is eluated by elution with 0.01M tris buffer containing 3 millimols of fructose-1,6-diphosphate. By the addition of solid ammonium sulfate up to a saturation of 0.5, the enzyme is precipitated. After centrifuging, the aldolase "A" is dissolved in 0.1M tris buffer, and the salting out process is twice repeated.

b. Isolation of Aldolase "B"

The following operations are conducted at 20° C.: 1,000 g. of human liver is comminuted in a meat grinder, mixed with 2.5 liters of 0.01M tris buffer, pH 7.5, and homogenized batchwise in a mixer for 5 minutes. The homogenate is centrifuged for 30 minutes at 13,000 g. By the addition of 1M tris buffer, pH 7.5, the molarity of the buffer in the effluent is increased to 0.05M, and 1 liter of calcium phosphate gel (50 mg/ml.) is added. The suspension is agitated for 1 hour, centrifuged, and the gel is discarded. The effluent is brought to a saturation of 0.3 with solid ammonium sulfate and worked up analogously to the method described under (2a), above, thus obtaining aldolase "B".

c. Isolation of Aldolase "C"

1,500 g. of human brain is homogenized batchwise in a mixer with 2.5 liters of ice-cold 0.01M tris buffer, pH 7.5, then centrifuged for 1 hour at 30,000 g. The clear supernatant is separated and brought to a saturation of 0.4 by the addition of solid ammonium sulfate. After 1 hour at 0° C., the mixture is centrifuged at 30,000 g. The supernatant is brought to a saturation of 0.7 by the addition of ammonium sulfate. The mixture is again centrifuged and the sediment dissolved in 300 ml. of 0.01M tris buffer, pH 7.5. A dialysis is conducted against several portions of the same buffer and the mixture charged on a DEAE-cellulose (diethylaminoethyl cellulose) column equilibrated with 0.01M tris buffer, pH 7.5, and washed with the same buffer until protein can no longer be detected in the eluate. During this step, aldolase A and the aldolase hybrid $A_3C$ are eluted. With the use of a linear sodium chloride gradient between 0 and 0.35M, and in the presence of 3 millimols of fructose-1,6-diphosphate, the mixture is eluted and all fractions with aldolase activity are collected. Then, the collected mixture is brought to a saturation of 0.7 with ammonium sulfate and centrifuged. The sediment is dissolved in 0.01M tris buffer, pH 7.5, and dialyzed for 24 hours against the same buffer. The dialyzate is charged onto a column with phosphocellulose, which has previously been equilibrated with the above buffer, and eluated with 0.2M tris buffer, pH 7.5, containing 3 millimols of fructose-1,6-diphosphate. The fractions with aldolase activity are salted out with ammonium sulfate. The resultant precipitate is separated by centrifuging, dissolved in 0.01M tris buffer, pH 7.5, and dialyzed for 24 hours against this buffer. The dialyzed solution is applied to a DEAE-cellulose column and eluted with a linear sodium chloride gradient between 0 and 0.3M, containing 3 millimols of fructose-1,6-diphosphate. The last fraction, containing the aldolase "C", is salted out with ammonium sulfate, centrifuged off, and the sediment dissolved in the buffer. The enzyme solution is then adjusted to an ammonium sulfate saturation of 0.55, during which step the aldolase "C" precipitates.

3. Purification of the Three Aldolase Types by Preparative Electrofocusing

The preparative purification by electrofocusing is conducted in a conventional apparatus and with a pH gradient of pH 7–10 (1% gel pH 7–10). The density gradient is adjusted with saccharose. Approximately 200 mg. of aldolase is used in a mixture with the density solution. At a voltage of 600 volts, the separating period amounts to 72 hours, at 0° C.

4. Crystallization

Small volumes (about 1 ml.) of aldolase "A", "B" and "C" (10 mg/ml.) are separately gradually mixed with saturated ammonium sulfate solution, until a slight turbidity is produced which is removed by centrifuging. The clear overflow is then gently provided with a layer of anhydrous n-butanol in silicone-treated test tubes (6 × 120 mm.) and allowed to stand about 10 days at 4°C.

In this manner, aldolase "A" is obtained as needle-shaped crystals of a specific activity of 5.50 U/mg. and a molecular weight of 160,000. Aldolase "B" is obtained as rhombic crystals with a specific activity of 0.95 U/mg. and a molecular weight of 162,000. Aldolase "C", in contrast thereto, does not crystallize but remains amorphous. The specific activity of this isozyme is 3.80 U/mg.; the molecular weight is 155,000.

5. Obtaining Antisera Against the Three Types of Aldolase

Antisera against aldolase "A", "B" and "C" are obtained by the immunization of turkey hens with one of these maximally pure aldolase isozymes. For this purpose, suitable amounts of a physiological sodium chloride solution and complete Freund adjuvant are combined in a ratio of 1:1, and the mixture is emulsified by ultrasonics until a stable water/oil emulsion has been formed. Thereafter, one of aldolase "A", "B" and "C" is added thereto and the emulsification is continued by hand. Turkey hens weighing 10–15 kg. are immunized with an amount of one of these emulsions corresponding to 5 mg. of antigen by intramuscular injection into the breast musculature. After six weeks, a secondary injection is effected into the wing vein with 5 mg. of the same aldolase isozyme in 3 ml. of physiological sodium chloride solution. Eight days later, about 200 ml. of blood per animal is withdrawn from the wing vein and filled into heparinized bottles. The blood is then centrifuged at 15,000 g. for 15 minutes, the plasma is freed of the fibrin by the addition of thrombokinase from rabbit brain and the thus-obtained serum is stored in the deep-frozen condition.

6. Determination of the Antibody Titer of the Thus-Obtained Antiserum

This determination is conducted with the aid of a "Heidelberger" curve. For this purpose, constant amounts of the antiserum are mixed with increasing quantities of one of the homologous antigens/aldolase "A", "B" and "C", and solid sodium chloride is added to a final concentration of 4%.

After incubation for one hour at 37° C. and a storage time of 2 hours in a refrigerator, the turbidities produced by immune precipitation are measured in a photometer at 436 nanometers using a 1 cm.-cuvette against a blank value. After removing the immune precipitate by centrifuging, the activity of the residual non-precipitated aldolase can be measured in the clear effluent.

In the experiments described hereinbelow, 1 ml. of the antisera anti-"A", anti-"B" and anti-"C", respectively was capable of precipitating completely 240 mU of aldolase "A", 100 mU of aldolase "B" and 160 mU of aldolase "C", respectively.

Determination of Aldolase Activities in Biological Fluids 2.5 ml. of a solution consisting of 4 millimols of fructose-1,6-diphosphate, 0.3 millimol of iodoacetate (sodium salt of monoiodoacetic acid), and 55 millimols of collidine buffer (0.55 millimols of collidine, adjusted to a pH of 7.4 with hydrochloric acid) is mixed with 0.05 ml. of a 15mM β-nicotinamide adenine dinucleotide solution and 0.01 ml. of a suspension consisting of 0.28 U/ml. of glycerin 3-phosphate dehydrogenase, 1.7 U/ml. of triose phosphate isomerase and 0.65 U/l. of lactate dehydrogenase in 2.8M ammonium sulfate solution. To this mixture is added 0.20 ml. of the serum to be tested, the solution is mixed, and maintained at +37° C. for 5 minutes. The extinction $E_1$ is measured against a blank value, and the mixture allowed to stand for exactly 20 minutes. Thereupon, the extinction $E_2$ is measured against a blank value. The blank value contains only 0.20 ml. of the serum to be examined and 2.5 ml. of 0.9% sodium chloride solution.

The aldolase content is calculated in accordance with the following formula:

$$\text{Volume Activity} = \frac{1000 \cdot V}{\epsilon \cdot d}(E_1 - E_2)/(t_2 - t_1) \, mU/ml.$$

wherein:

| | | |
|---|---|---|
| V | = | test volume |
| ε | = | extinction coefficient (cm²/μmol) |
| d | = | layer thickness (cm) |
| $(t_2 - t_1)$ | = | measuring time interval (minutes) |

C. Determination of the Content of the Aldolase Isozymes in Raw Extracts of Human Organs One milliliter of a human skeletal muscle raw extract with an aldolase activity of 40.8 mU/ml. is mixed with 1 ml. of an anti-"A" (anti-aldolase-"A") serum, and the final concentration of sodium chloride is adjusted to 4%. The mixture is incubated at 37° C. for 60 minutes and then stored for 2 hours at +4° C. After centrifuging off the immune precipitate at 20,000 g., the aldolase activity of the supernatant is determined in accordance with the above-disclosed aldolase detection method. This activity is 1.5 mU (3.7% of the original serum activity).

Analogously, with 1 ml. of anti-"B" or anti-"C", the aldolase "B" and aldolase "C", respectively, are precipitated from other 1 ml. portions of the same skeletal muscle raw extract and the remaining residual aldolase activity in the supernatant is determined. This residual aldolase activity is 41.2 mU for anti-"B" and 42.05 mU for anti-"C". Thus, in both cases, practically all of the aldolase activity has been retained in the skeletal muscle raw extract and practically none has been precipitated.

From these values, the following distribution of the aldolase isozymes in the human skeletal muscle is obtained:

| Aldolase A | 96.3% |
|---|---|
| B | 0% |
| C | 0% |

Analogously, the percentage content of the aldolase isozymes in the raw extract of other human organs was determined:

| Aldolase | "A" | "B" | "C" |
|---|---|---|---|
| Liver | 1 | 98 | 0 |
| Myocardium | 80 | 11 | 27 |
| Brain | 84 | 0 | 54 |
| Lung | 76 | 27 | 22 |
| Kidney | 20 | 75 | 5 |
| Spleen | 91 | 0 | 13 |
| Testis | 92 | 1 | 18 |
| Skin | 33 | 73 | 0 |
| Erythrocytes | 96 | 0 | 16 |
| Spermatozoa | 97 | 5 | 35 |

It can be seen that the akeletal musculature contains almost exclusively aldolase "A", whereas the liver contains only type "B". The brain, spleen, tests and the erythrocytes contain aldolase "A" and "C", the skin contains types "A" and "B", and in the other organs, all three types are present in varying proportions.

In some organs and tissues, values are obtained in the addition which are larger than 100%. The reason for this is that hybrids are also present in addition to the pure enzyme types.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Diagnosis of Muscular Dystrophy

One milliliter of an erythrocyte-free serum having a total aldolase activity of 64.2 mU/ml. is mixed with 2 ml. of the anti-"A" serum produced in accordance with the abovedescribed method, and brought to a final NaCl concentration of 2.5% with 10% sodium chloride solution. Thereafter, the mixture is incubated at 37° C. for one hour and subsequently stored for 3 hours at +4° C. After centrifuging off the precipitate at 20,000 g. during a period of 10 minutes, the aldolase activity is determined according to the aforedescribed determination method. The activity is 5.4 mU (8.4% of the original serum activity).

Analogously, with 1 ml. of anti-"B" or anti-"C", the existing proportion of aldolase "B" or aldolase "C", respectively is precipitated from other one-ml. samples of the same serum and the remaining residual total aldolase activity is determined in the effluent. This activity is 62.0 mU for anti-"B" and 60 mU for anti-"C". In the serum, there have thus been preserved 96.5% and 93.5%, respectively, of the original aldolase activity.

From these values, the following distribution of the three aldolase isozymes results:

|  | Muscular Dystrophy Patient A | Normal Patient |
|---|---|---|
| Aldolase A | 91.6 | 79.2 |
| B | 3.5 | 17.0 |
| C | 6.5 | 8.5 |

Compared with the normal values, a pronounced increase in aldolase "A" proportion is observed, which establishes the presence of progressive muscular dystrophy. This diagnosis can be confirmed by clinical investigations.

In analogous determinations with the sera of two further patients (B and C), the following percentage distributions of the aldolase isozymes were detected:

|  | Patient B | Patient C |
|---|---|---|
| Aldolase A | 86.4 | 96.9 |
| B | 3 | 3.2 |
| C | 9 | 1 |

These results establish that muscular dystrophy exists in these patients, as could be confirmed by clinical methods of examination.

EXAMPLE 2

Diagnosis of Infectious Hepatitis

One milliliter of a serum having a total aldolase activity of 21.8 mU/ml. is mixed with 0.3 ml. of an antiserum anti-"A". In two further samples, 0.5 ml. of anti-"B" and 0.3 ml. of anti-"C", respectively, is added. The isozyme determination is then conducted analogously to Example 1. The results of this series of tests and 2 further test series with other sera are compiled in the following table:

| Serum | Serum Activity in U/ml. | Antiserum Type | Antiserum (ml.) | Activity of Effluent in mU | in % of Serum Activity | Aldolase Activity in % of Serum Activity |
|---|---|---|---|---|---|---|
| I | 21.8 | Anti-A | 0.3 | 19.2 | 88.2 | A: 11.8 |
|  | 21.8 | Anti-B | 0.5 | 1.75 | 8.05 | B: 91.95 |
|  | 21.8 | Anti-C | 0.3 | 21.8 | 100 | C: 0 |
| II | 18.8 | Anti-A | 0.5 | 17.6 | 93.5 | A: 6.5 |
|  | 18.8 | Anti-B | 0.5 | 1.8 | 9.6 | B: 90.4 |
|  | 18.8 | Anti-C | 0.5 | 17.5 | 93.0 | C: 6.0 |
| III | 24.7 | Anti-A | 1.0 | 22.6 | 91.5 | A: 8.5 |
|  | 24.7 | Anti-B | 1.0 | 1.8 | 7.3 | B: 92.7 |
|  | 24.7 | Anti-C | 1.0 | 24.2 | 98.0 | C: 2 |
| Normal Serum | 2.4 | Anti-A | 0.3 | 0.5 | 20.8 | A: 79.2 |
|  | 2.4 | Anti-B | 0.3 | 2.0 | 83 | B: 17.0 |
|  | 2.4 | Anti-C | 0.3 | 2.2 | 91.5 | C: 8.5 |

The high values of aldolase "B" establishes the presence of infectious hepatitis.

This diagnosis could be proven by clinical investigations.

EXAMPLE 3

Diagnosis of Myocardial Infarction

Analogously to the method of determination of Examples 1 and 2, five different sera were diagnosed, and the following results were obtained:

| Serum | Serum Activity in U/ml. | Antiserum Type | Antiserum (ml.) | Activity of Effluent in mU | in % of Serum Activity | Aldolase Activity in % of Serum Activity |
|---|---|---|---|---|---|---|
| I | 58.4 | Anti-A | 0.6 | 23.45 | 40.0 | A: 60 |

| Serum | Serum Activity in U/ml. | Anti-serum Type | Anti-serum (ml.) | Activity of Effluent in mU | Activity of Effluent in % of Serum Activity | Aldolase Activity in % of Serum Activity |
|---|---|---|---|---|---|---|
|  | 58.4 | Anti-B | 0.6 | 22.6 | 38.7 | B: 61.3 |
|  | 58.4 | Anti-C | 0.6 | 42.9 | 73.5 | C: 26.5 |
| II | 21.0 | Anti-A | 0.5 | 4.3 | 20.5 | A: 79.5 |
|  | 21.0 | Anti-B | 0.5 | 18.1 | 86.2 | B: 13.8 |
|  | 21.0 | Anti-C | 0.5 | 17.6 | 84.0 | C: 16.0 |
| III | 18.8 | Anti-A | 0.5 | 3.8 | 20.2 | A: 79.8 |
|  | 18.8 | Anti-B | 0.5 | 15.2 | 81.0 | B: 19.0 |
|  | 18.8 | Anti-C | 0.5 | 13.9 | 74.0 | C: 26.0 |
| IV | 6.8 | Anti-A | 0.2 | 1.7 | 25.0 | A: 75.0 |
|  | 6.8 | Anti-B | 0.2 | 5.0 | 73.4 | B: 26.6 |
|  | 6.8 | Anti-C | 0.2 | 6.1 | 89.8 | C: 10.2 |
| V | 6.8 | Anti-A | 0.3 | 1.9 | 28.0 | A: 72.0 |
|  | 6.8 | Anti-B | 0.3 | 5.5 | 81.0 | B: 19.0 |
|  | 6.8 | Anti-C | 0.3 | 5.7 | 84.0 | C: 16.0 |
| Normal Serum | 2.4 | Anti-A | 0.3 | 0.5 | 20.8 | A: 79.2 |
|  | 2.4 | Anti-B | 0.3 | 2.0 | 83 | B: 17.0 |
|  | 2.4 | Anti-C | 0.3 | 2.2 | 91.5 | C: 8.5 |

The increased values of aldolase "C" and/or the aldolase activity values which frequently lie above 100% establish the presence of a cardiac infarction.

These diagnoses could be confirmed by further clinical tests.

EXAMPLE 4

Test Kit for Determining the Isozyme Pattern of Aldolase

Components:
1. Three small bottles containing
   a. 10 ml. of anti-"A" serum (1 ml. precipitates about 240 mU of aldolase)
   b. 5 ml. of anti-"B" serum (1 ml. precipitates about 100 mU of aldolase)
   c. 5 ml. of anti-"C" serum (1 ml. precipitates about 160 mU of aldolase)
(2) Complete set of reagents for determining aldolase activity (for about 25 determinations), consisting of:
   a. 80 ml. of buffer substrate solution (55 mM collidine buffer, pH 7.4; 3 mM fructose 1,6-diphosphate; 0.3 mM of iodoacetate)
   b. 30 mg. of NADH$_2$ disodium salt, lyophilized
   c. 1 ml. of a 2.8M ammonium sulfate solution containing: 0.25 – 0.30 U glycerin 3-phosphate dehydrogenase 1.5 – 2.0 U triose phosphate isomerase 0.5 – 1.0 U lactate dehydrogenase
   d. 80 ml. of physiological sodium chloride solution The NADH$_2$ is dissolved in 2 ml. of twice-distilled water; all other reagents are ready for use.

EXAMPLE 5

Hexokinase a. Isolation and Purification of Hexokinase Isozymes

From human organs, e.g., heart, kidney, lung, spleen, liver, two isozymes of hexokinase, called "HK I" and "HK III", are isolated analogously to the above-described methods, and purified until they are uniform from an electrophoretic and immunological viewpoint. Besides these two isolated, defined isozymes, there remains in some tissues a hexokinase residual activity which perhaps relates to several further isozymes. This residual activity is temporarily designated "UI" (unidentified).

b. Preparation of the Antibodies Against Hexokinase Isozymes "HK I" and "HK III"

Analogously to the aforedescribed methods, antisera are produced against the two above-mentioned isozymes by twofold immunization of turkey hens either with an emulsion of "HK I" or with "HK III", respectively, with Freund adjuvant.

In this procedure, an amount of emulsion is employed in each case which corresponds to 10 mg. of the two pure isozymes. The antibody titer is determined with the aid of a "Heidelberger" curve. Respectively 1 ml. of the antisera anti-"HK I" and anti-"HK III" precipitate 80 mU of hexokinase I and 65 mU of hexokinase III, respectively.

c. Determination of Hexokinase Activity in Biological Fluids

The determination is conducted according to the method described by Th. Buecher, W. Luh, and D. Pette in Hoppe-Seyler/Thierfelder: "Handbuch der physiologischen und pathologisch-chemischen Analyse", Springer publishers, 1964, Vol. SVI, p. 318.

d. Distribution Pattern of Hexokinase Isozymes in Human Organs

From various human organs, raw extracts are prepared by homogenization in ice-cold tris buffer, pH 7.5. In the clear raw extract, the hexokinase activity is determined according to the method described in (c), above. Thereafter, 1 ml. portions of the extract is mixed with one of the following:

1. 0.5 ml. of anti-"HK I"
2. 0.5 ml. of anti-"HK III"
3. 0.5 ml. of anti-"HK I" and 0.5 ml. of anti-"HK III"

In all samples, the NaCl final concentration is brought to 4%.

After incubation and centrifuging as described above, the hexokinase activity is once again determined in the effluent of the three serum samples (1), (2) and (3). The thus-obtained values yield the following distribution of the hexokinase isozymes in the tissues:

| Organ | "HK I" | "HK III" | "U I" | Sum of Activities (in %) |
|---|---|---|---|---|
| Heart | 98 | 0 | 0 | 98 |
| Kidney | 81 | 0 | 19 | 100 |
| Lung | 78 | 17 | 2 | 97 |
| Spleen | 49 | 43 | 10 | 102 |
| Liver | 28 | 55 | 20 | 103 |

By determining the isozyme pattern in sera of patients having various diseases, and comparing with the isozyme pattern of the serum of normal persons, organ-specific and/or disease-specific differential diagnoses can be rendered for various diseases, in the same manner described in connection with aldolase.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the quantitative determination of at least one diagnostically relevant isozyme form of a human enzyme occuring in a plurality of genically defined, immunologically differentiatable multiple isozyme forms, which comprises:
    a. quantitatively measuring the total enzyme activity of said multiple isozyme forms in a human body fluid, tissue extract or excretion sample;
    b. admixing a portion of said sample with a two to ten fold theoretical excess of a precipitating antibody against a homologous diagnostically relevant human isozyme form, which antibody is specific to said diagnostically relevant human isozyme form and is substantially free of immunological activity against other of said multiple isozyme forms, to produce a substantially quantitative antigen-antibody immunoprecipitin complex consisting essentially of said diagnostically relevant human isozyme form and said antibody;
    c. substantially quantitatively separating said immunoprecipitin complex from the resultant admixture so that at least 90% of the diagnostically relevant human isozyme form activity is removed therefrom; and
    d. quantitatively measuring the total enzyme activity of the remaining multiple isozyme forms substantially free of the diagnostically relevant human isozyme form, whereby the diagnostically relevant human isozyme form can be quantitatively determined.

2. A process according to claim 1 wherein the enzyme is aldolase, hexokinase, creatine kinase or lactate dehydrogenase.

3. A process according to claim 1 wherein the enzyme is aldolase and the aldolase A, aldolase B and aldolase C contents of the sample are determined.

4. A process according to claim 1 wherein the enzyme is hexokinase and the HK I and HK III hexokinase isozyme contents of the sample are determined.

5. A process according to claim 1 wherein there is added to aliquots of the sample an amount of antisera against each diagnostically relevant isozyme of the selected enzyme in an excess up to 10 times of the theoretical amount of the antiserum required to form an isozyme-antibody complex with all of that maximum isozyme which could be present in the aliquot, the resulting precipitates are separated and the isozyme content of the sample determined by measuring the residual total enzyme activity for each aliquot after the formation of the specific isozyme-antibody complex.

6. A process according to claim 1 wherein the mixture of sample and antisera are incubated for up to 5 hours before separating the precipitated isozyme-antibody complex.

7. A process according to claim 1, wherein the enzyme is selected from the group consisting of kinases, transaminases, dehydrogenases, phosphatases, proteases, hydrolases, and nucleotidases.

8. A process according to claim 7, wherein the enzyme is a kinase.

9. A process according to claim 8, wherein the kinase is creatinine kinase.

10. A process according to claim 8, wherein the kinase is hexokinase.

11. A process according to claim 7, wherein the enzyme is a transaminase.

12. A process according to claim 11, wherein the transaminase is alanine aminotransferase or aspartate aminotransferase.

13. A process according to claim 7, wherein the enzyme is a dehydrogenase.

14. A process according to claim 13, wherein the dehydrogenase is lactate dehydrogenase.

15. A process according to claim 7, wherein the enzyme is a phosphatase.

16. A process according to claim 15, wherein the phosphatase is alkaline phosphatase.

17. A process according to claim 1, wherein the enzyme is a peptidase.

18. A process according to claim 1, wherein the enzyme is a protease.

19. A process according to claim 7, wherein the enzyme is a hydrolase.

20. A process according to claim 19, wherein the hydrolase is amylase.

21. A process according to claim 1, wherein the enzyme is an esterase.

22. A process according to claim 7, wherein the enzyme is a nucleotidase.

* * * * *